(12) United States Patent
Cross, Jr. et al.

(10) Patent No.: US 7,996,090 B2
(45) Date of Patent: Aug. 9, 2011

(54) METHODS OF MAKING IMPLANTABLE MEDICAL LEADS WITH A NON-LINEAR SHAPE

(75) Inventors: Thomas E. Cross, Jr., St. Francis, MN (US); Michaelene M. Williams, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 1102 days.

(21) Appl. No.: 11/742,449

(22) Filed: Apr. 30, 2007

(65) Prior Publication Data

US 2008/0269860 A1 Oct. 30, 2008

(51) Int. Cl.
*A61N 1/05* (2006.01)
(52) U.S. Cl. ......... 607/116; 607/117; 607/122; 607/123
(58) Field of Classification Search .......... 607/116–117, 607/122–123
See application file for complete search history.

(56) References Cited

U.S. PATENT DOCUMENTS

| | | | |
|---|---|---|---|
| 3,333,045 A * | 7/1967 | Fisher et al. | 174/20 |
| 4,154,247 A | 5/1979 | O'Neill | |
| 4,289,144 A | 9/1981 | Gilman | |
| 4,458,677 A | 7/1984 | McCorkle, Jr. | |
| 4,567,901 A * | 2/1986 | Harris | 607/123 |
| 5,086,787 A | 2/1992 | Grandjean et al. | |
| 5,628,779 A | 5/1997 | Bornzin et al. | |
| 5,772,693 A | 6/1998 | Brownlee | |
| 5,922,014 A * | 7/1999 | Warman et al. | 607/123 |
| 5,967,977 A | 10/1999 | Mullis et al. | |
| 6,066,165 A | 5/2000 | Racz | |
| 6,434,431 B1 | 8/2002 | Camps et al. | |
| 6,574,512 B1 | 6/2003 | Zhang et al. | |
| 6,587,733 B1 | 7/2003 | Cross, Jr. et al. | |
| 6,843,870 B1 | 1/2005 | Bluger | |
| 2002/0116042 A1 | 8/2002 | Boling | |
| 2003/0139794 A1 * | 7/2003 | Jenney et al. | 607/122 |
| 2005/0016657 A1 | 1/2005 | Bluger | |
| 2005/0033394 A1 | 2/2005 | Seifert et al. | |
| 2005/0203599 A1 | 9/2005 | Garabedian et al. | |
| 2006/0032657 A1 | 2/2006 | Zarembo | |
| 2007/0282410 A1 | 12/2007 | Cross, Jr. et al. | |

(Continued)

FOREIGN PATENT DOCUMENTS

DE 10 2004 035 002 A 2/2006

(Continued)

OTHER PUBLICATIONS

PCT Search Report (mailed Nov. 6, 2007); 11 pgs.

(Continued)

*Primary Examiner* — Carl H Layno
*Assistant Examiner* — Jennifer Stewart

(57) ABSTRACT

Implantable medical leads and methods of making. The method includes providing first and second tubes, and arranging a segment of the first tube side-by-side with a segment of the second tube along a region of interface. The tubes are forced to a non-linear shape along at least a portion of the region of interface. An adhesive is applied to the portion of the region of interface and cured. Upon curing, the adhesive bonds the tubes to one another and elastically maintains the non-linear shape in the absence of an external force. A conductive element is disposed within at least one of the tubes. In some embodiments, the non-linear shape is a sigmoid shape, and the method includes arranging the tube segments in a fixture having a structure defining the sigmoid shape.

2 Claims, 7 Drawing Sheets

U.S. PATENT DOCUMENTS

| | | |
|---|---|---|
| 2008/0039917 A1 | 2/2008 | Cross, Jr. et al. |
| 2008/0046058 A1 | 2/2008 | Cross, Jr. et al. |
| 2008/0051861 A1 | 2/2008 | Cross, Jr. et al. |
| 2008/0269837 A1 | 10/2008 | Ludlow et al. |
| 2008/0269856 A1 | 10/2008 | Cross, Jr. et al. |
| 2008/0269857 A1 | 10/2008 | Cross, Jr. et al. |
| 2008/0269858 A1 | 10/2008 | Cross, Jr. et al. |
| 2008/0269859 A1 | 10/2008 | Cross, Jr. et al. |
| 2008/0269861 A1 | 10/2008 | Cross, Jr. et al. |

FOREIGN PATENT DOCUMENTS

| | | |
|---|---|---|
| DE | 10 2004 035 002 A1 | 2/2006 |
| EP | 0 057 448 A1 | 8/1982 |
| EP | 0 057 448 A1 | 11/1982 |
| EP | 0 657 185 A2 | 6/1995 |
| WO | 99/30772 | 6/1999 |
| WO | 2004/035133 | 4/2004 |

OTHER PUBLICATIONS

PCT Search Report mailed Feb. 4, 2008; 8 pgs.
PCT Search Report (mailed Jan. 3, 2008); 6 pgs.
PCT Search Report mailed Nov. 14, 2007; 8 pgs.
PCT Search Report mailed Jan. 2, 2008 (6 pgs.).
PCT Search Report mailed Oct. 29, 2007; 15 pgs.

* cited by examiner

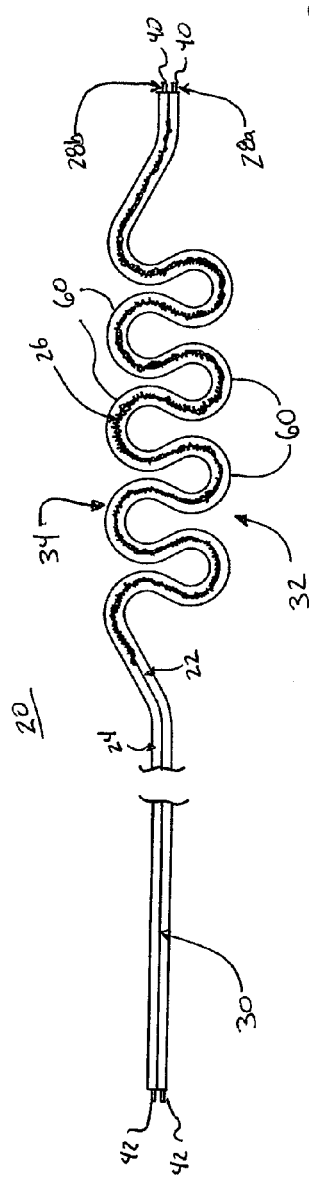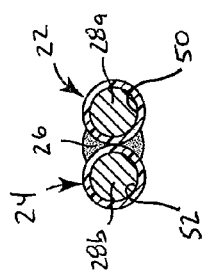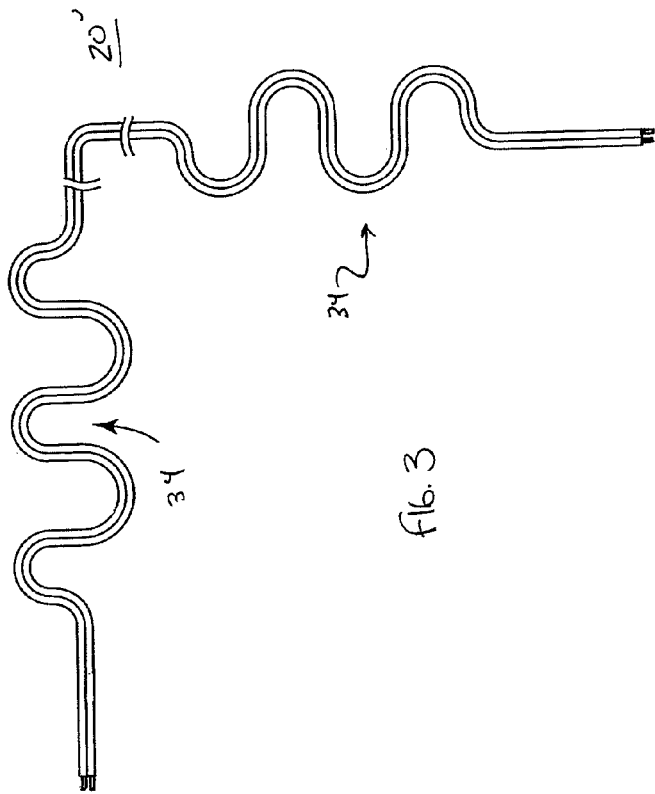

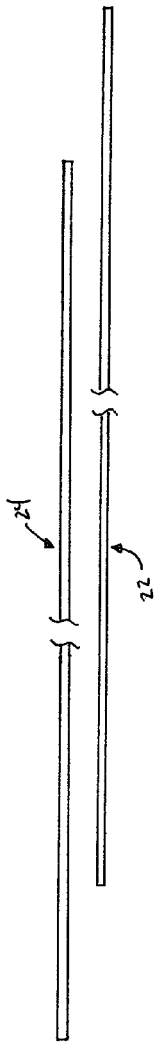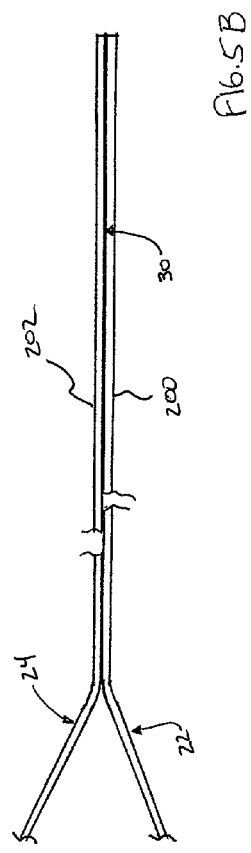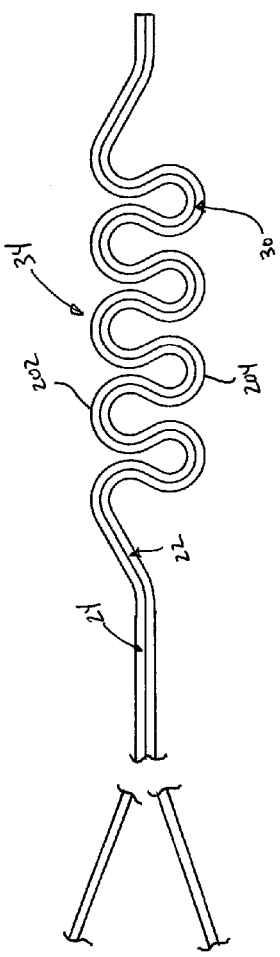

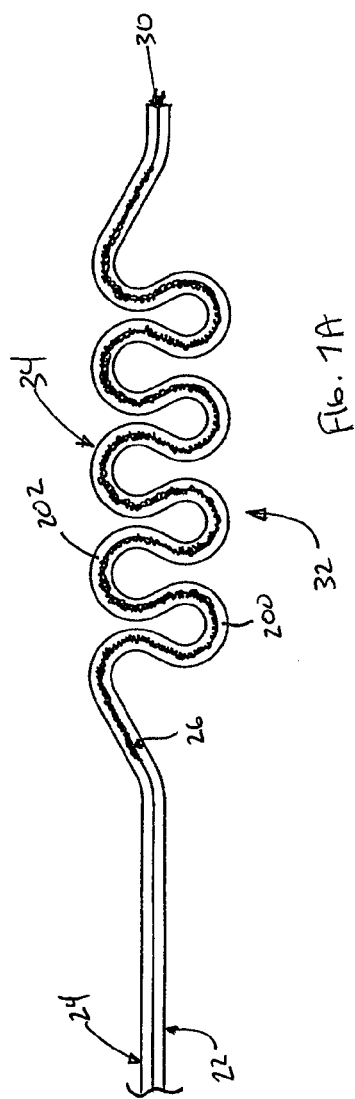
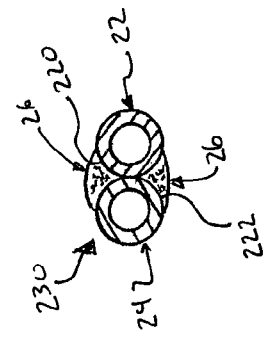
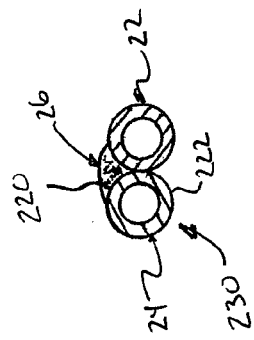
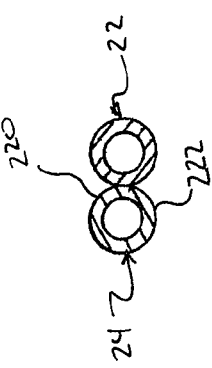

METHODS OF MAKING IMPLANTABLE MEDICAL LEADS WITH A NON-LINEAR SHAPE

BACKGROUND

The present invention relates to implantable medical leads for connection between a stimulating control device and one or more stimulation or sensing electrodes and methods of manufacturing such leads, and more particularly to methods of manufacturing flexible and extensible implantable medical leads.

Systems and methods for electrical stimulation of electrically excitable tissue within the body of a living subject have been developed utilizing stimulating electrodes and a signal generator or control device to supply electrical charges in a controlled or predetermined manner. Such systems and methods have been developed specifically based upon a desired condition, such as to alleviate pain or to stimulate muscle movement, and based upon the application with a subject's body. For bodily applications where the alleviation of pain is the goal, one or more stimulating and/or sensing electrodes can be implanted within nerve tissue, the brain or spinal cord for blocking pain sensation by electrical stimulation. For muscle tissue stimulation, a stimulating electrode can be implanted in a muscle tissue, whereby electrical current that is typically provided as pulses can cause muscle tissue reaction that may be controlled to cause movement of a subject's body part. Sensing electrodes are used for determining actions of the body.

Signal generators can determine when, how long, and/or the amperage of current pulses that are to be applied for the specific application, and often include hard-wired circuitry, a microprocessor with software and/or embedded logic as the controlling system for determining and dictating current pulses. Such signal generators may also be implanted within the subject's body, and typically such an implantation is done to position the signal generator close to the stimulating and/or sensing electrodes, with interconnecting medical leads for conducting current pulses to and from the stimulating and sensing electrodes. Implantable medical leads and externally utilized leads for these purposes are typically insulated conductors or conductive elements (e.g., a conductor disposed within a lead body), with conductive terminations at both ends for electrical connection with the signal generator and one or more electrodes. Implantable medical leads further have requirements for safe interbody use such as tissue compatibility, surgical procedure dynamics, and body fluid accommodation.

Signal generation and muscle tissue stimulation systems have more recently been envisioned for more complex control of a subject's bodily actions. One particularly complex muscular control concept has recently been considered for the purpose of re-teaching a subject how to swallow, the condition of inability to swallow being known as dysphagia. Techniques and methods of stimulating muscles within the neck region of a patient for the purposes of causing specifically determined muscles to react as a swallowing effect are described in PCT Publication No. WO 2004/028433, having a publication date of Apr. 8, 2004. Specifically, by implanting electrodes in two or more muscles of the upper airway musculature and connecting the electrodes with a signal generator that provides coordinate control signals, a swallowing action can be induced in the patient. Other specific techniques and methods are also disclosed in U.S. Pat. Nos. 5,725,564; 5,891,185; 5,987,359; 6,104,958; and 6,198,970; all to Freed et al. Other techniques and methods are disclosed in U.S. patent application Ser. No. 11/611,365, filed Dec. 15, 2006, and entitled "Method and Apparatus for Assisting Deglutition." The teachings of each of these references are incorporated herein by reference in their entireties.

For these and other implanted electrode stimulation treatments, conventional leads may not be optimal. For example, a lead implanted (e.g., tunneled) from the patient's chest (e.g., from a stimulation signal generator) to the neck (and thus within tissue of the neck) should allow for the patient's head and neck to perform natural movements (including gross movements such as turning, raising and lowering of the head, etc.), as well as fine movements such as those associated with swallowing. Other bodily regions present similar movement concerns or constraints. With this in mind, and as mentioned above, medical leads include a conductor or conductive element maintained by a lead body (e.g., an insulative covering) with conductive terminations at the ends thereof for electrical connection to other components of the treatment system, such as a signal generator, electrode(s) (e.g., a stimulation electrode, a sensing electrode, etc.) and/or a lead extension. To this end, conventional leads typically exhibit limited longitudinal extensibility (e.g., will not longitudinally "stretch"). As such, when implanted in bodily regions that are normally subjected to movement by the patient, such movements can impart a tension-type force onto the lead (e.g., a lead running from the chest to a muscle or other tissue in the patient's neck will be subjected to a tensioning force with movement (such as tilting) of the neck/head). Due to the limited extensibility of conventional leads, the lead cannot accommodate the desired movement, but instead may overtly resist the tension force. This resistance, in turn, limits the ability of the patient to physically perform the desired movement.

Providing extra length or "slack" in a lead's length as it is connected between a signal generator and an electrode could potentially accommodate physical movements. However, the flexibility of such a lead would initially and uncontrollably allow lead portions to sag or collect within bodily cavities, spaces between tissue layers, etc. Moreover, if lead slack were to gather in a bodily cavity and/or between tissue, lead extension may then be limited or uncomfortable as the lead may slide or be pulled through tissue layers, or from the bodily cavity, in connection with physical movement of the bodily region in question. Resultant discomfort and/or pain can have the effect of limiting the patient's normal movements to the same extent as described above, as the patient will consciously or sub-consciously decide not to perform uncomfortable movements. Also, after a lead is implanted for some time, the lead begins and gradually adheres to one or more of the adjacent tissue, particularly in area(s) of lead sag or collection of excess lead material. As a result, the extra length of any such lead would no longer be available to permit desired extension (in otherwise accommodating desired movement of the bodily region in question).

In light of the above, a need exists for a lead configuration exhibiting enhanced flexibility and extensibility, and methods of making such leads.

SUMMARY

Some aspects in accordance with the present disclosure relate to methods of making an implantable lead. The method includes providing first and second tubes, and arranging a segment of the first tube side-by-side with a segment of the second tube along a region of interface. The tubes are forced to a non-linear shape along at least a portion of the region of interface. An adhesive is applied to the portion of the region of interface, and cured. Upon curing, the adhesive bonds the tubes to one another and elastically maintains the non-linear shape in the absence of an external force. A conductive element is disposed within at least one of the tubes. In some embodiments, the non-linear shape is a sigmoid shape, and the method includes arranging the tube segments in a fixture having a structure defining the sigmoid shape and subjecting the portion of the region of interface to a temperature above ambient to promote curing of the adhesive. In other embodiments, the adhesive is separately applied to both opposing major faces defined by the region of interface. In yet other embodiments, the conductive element is disposed within one of the first and second tubes after curing the adhesive, and in other embodiments is disposed prior to curing of the adhesive.

Yet other aspects in accordance with the present disclosure relate to an implantable medical lead including a first tube, a second tube, an adhesive, and at least one conductive element. The tubes are arranged side-by-side, and the adhesive is cured to bond the tubes to one another along at least a portion of a region of interface. In this regard, the portion of the region of interface has a non-linear shape, and the cured adhesive substantially maintains the non-linear shape in the absence of an external force. Finally, the conductive element is disposed within at least one of the first and second tubes. With this construction, the implantable medical lead is longitudinally flexible and extensible in that the non-linear shape is longitudinally, elastically deformable or extensible in the presence of a longitudinal tensioning force (e.g., the non-linear shape transitions toward a more straightened shape), and self-transitions to the non-linear shape upon removal of the tensioning force. In this regard, the cured adhesive imparts a tensile strength to the non-linear shape portion of the lead in establishing a shape memory.

BRIEF DESCRIPTION OF THE DRAWINGS

FIG. 1 is a side view of an implantable medical lead in accordance with aspects of the present disclosure;

FIG. 2 is a cross-sectional view of the lead of FIG. 1;

FIG. 3 is a side view of an alternative implantable medical lead in accordance with aspects of the present disclosure;

FIGS. 5A-5C illustrate portions of the methods of FIG. 4;

FIGS. 7A-7D illustrate further portions of the methods of FIG. 4; and

DETAILED DESCRIPTION

Figure 4:
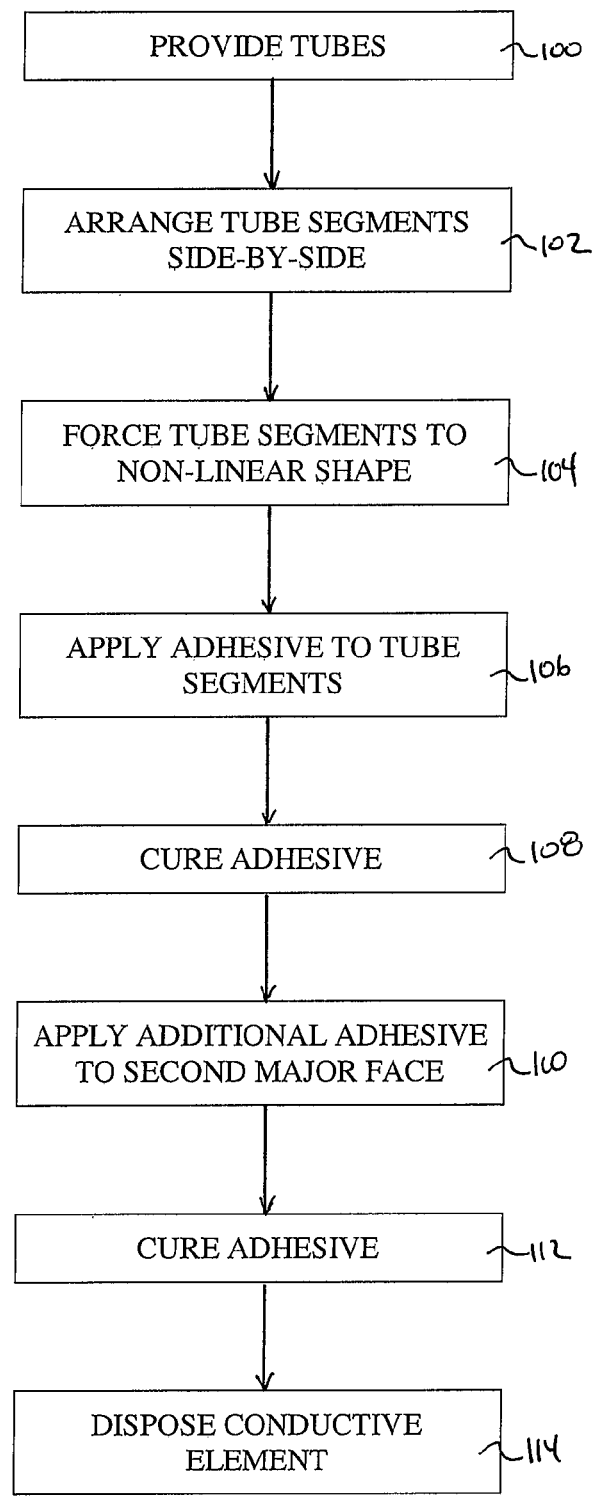
FIG. 4 is a flow diagram illustrating methods in accordance with aspects of the present disclosure, for making an implantable medical lead, such as the lead of FIG. 1.

One embodiment of a lead 20 in accordance with aspects of the present disclosure is shown in FIG. 1. The lead 20 can assume a variety of forms, and includes a first tube 22, a second tube 24, adhesive 26 (referenced generally), and one or more conductive elements or conductors 28a, 28b. Details on the various components are provided below. In general terms, however, at least a segment of each of the first and second tubes 22, 24 are arranged side-by-side along a region of interface 30. At least a portion 32 of the region of interface 30 has a non-linear shape 34. The adhesive 26 bonds the tubes 22, 24 along the portion 32, and substantially maintains the non-linear shape 34 in the absence of an external force. In other words, in the absence of a tensioning force (e.g., longitudinal pulling force) being applied to the lead 20 (or other no-load condition), the portion 32 elastically retains the non-linear shape 34 due, at least in primarily, to the cured adhesive 26. Finally, the first conductive element 28a is disposed within the first tube 22 and, where provided, the second conductive element 28b is disposed within the second tube 24. With this configuration, under a no-load condition, the portion 32 of the lead 20 will assume the non-linear shape 34, but which shape 34 is elastically deformable and will return to the no-load, non-linear shape 34 once the load is removed. This feature, in turn, provides for controlled extensibility of the lead 20 under expected load conditions following implant.

The tubes 22, 24 can assume a variety of forms as known in the implantable medical lead art (e.g., polymer-type tubings), and may or may not be identical. In some embodiments, the tubes 22, 24 are each formed of a silicone rubber material, although other materials selected to exhibit one or more properties desired for a particular implant application or procedure (e.g., softness, lubricity, etc.) are also acceptable. Regardless, the selected material(s) for the tubes 22, 24 is compatible with the selected composition of the adhesive 26 in effectuating a strong bond between the adhesive 26 and the tubes 22, 24 as described below. Further, the material(s) of the tubes 22, 24, and related wall thicknesses (which may or may not be identical and/or uniform for the two tubes 22, 24) and tensile strength (which may or may not be identical for the two tubes 22, 24) are selected, in some embodiments, to readily assume the non-linear shape 34 when subjected to a shaping force or forces during manufacture of the lead 20 as described below. Finally, while the tubes 22, 24 are described below as preferably forming a lumen (shown in FIG. 2, for example), in other embodiments, one or both of the tubes 22 and/or 24 are solid.

The adhesive 26 can also assume a variety of forms, and is preferably formed of surgically compatible material(s). Further, the adhesive 26 composition is selected in accordance with material(s) of the tubes 22, 24 for effectuating a strong bond in holding the two tubes 22, 24 two one another following manufacture. Finally, and in accordance with some embodiments, the selected adhesive 26 exhibit liquid or semi-liquid or flowable characteristic in a first, solution state (e.g., prior to application to the tubes 22, 24), and a hardened or cured characteristic in a second, cured state in bonding the tubes 22, 24. One acceptable composition of the adhesive 26 is a silicone adhesive, although other forms are also acceptable.

The conductive element(s) 28a and/or 28b can be identical, each forming or defining conductive lead terminations 40, 42 that are electrically coupleable to one or more components of an implantable electrical stimulation and/or sensing system (e.g., electrode(s), lead extender, stimulation control unit or generator, etc.). In this regard, the conductive elements 28a, 28b can comprise any known or developed conductive wire or the like that may be a solid element (e.g., shaft, coil, etc.), and/or be comprised as a stranded conductor as such are well-known. Stranded wire as used for the conductive element 28a, 28b would typically be more flexible as compared with solid wire. However, a solid wire is typically more capable of being deformed to hold a shape and can exhibit a spring-back characteristic that may be useful with leads in accordance with some embodiments of the present disclosure. The lead terminations 40, 42 can comprise any known or developed electrical connection that may be appropriate for connection between other electronic components depending on the specific applications. For example, the lead termination(s) 40 and/or 42 may be merely uninsulated wire portions for connection with other electrical connectors, or may comprise the connectors themselves as fixed to the end(s) of the conductive element(s) 28a and/or 28b. One or both of the conductive elements 28a and/or 28b can be flexible so as to not be capable of itself defining the desired non-linear shape 34, or can be configured to exhibit a shape memory characteristic.

While FIGS. 1 and 2 reflects the first conductive element 28a within the first tube 22 and the second conductive element 28b within the second tube 24, in other embodiments, two or more of the conductive elements 28a or 28b can be provided with the first tube 22 and/or the second tube 24, and can be insulated from one another in a conventional manner (e.g., by insulation material coating). Conversely, in other embodiments, only one of the conductive elements 28a or 28b is provided (e.g., the first conductive element 28a is provided within the first tube 22, and the second conductive element 28b is omitted such that the second tube 22 is free of any conductive elements). Further, while the first tube 22 is illustrated in FIG. 2 as forming or defining a lumen 50 and the second tube 24 forms or defines a lumen 52 within which the respective conductive elements 28a, 28b are disposed, in other embodiments, the first tube 22 and/or the second tube 24 need not form or define a lumen. For example, the first tube 22 can encompass the first conductive element 28a within a material thickness of the first tube 22 (e.g., the first tube 22 can be molded to the first conductive element 28a that otherwise is provided in coil form, etc.). The second tube 24 may or may not be similarly constructed relative to the second conductive element 28b.

As described in greater detail below, methods of manufacturing the lead 20 in accordance with aspects of the present disclosure readily impart the non-linear shape 34 to the portion 32, with the adhesive 26, upon curing, serving to substantially retain the non-linear shape 34 in an elastically deformable manner (i.e., the lead 20 can transition from the non-linear shape 34 to a more straightened shape in response to an external force, and then self-transition back toward the non-linear shape 34 upon removal of the force). With this in mind, the non-linear shape 34 can assume a wide variety of forms. In general terms, the non-linear shape 34 has or is characterized by, in some embodiments, a plurality of curves or curved sections 60. The curves 60 can be formed to define a repetitive pattern as shown in FIG. 1, or can have a more random distribution/shape along a longitudinal length of the lead 20. In some embodiments, the non-linear shape 34 is a sigmoid shape (e.g., a pattern of repeating, back-and-forth curves 60 that may or may not extend back toward one another). Even further, the two or more distinct or discrete portions of non-linear shape can be provided, as shown, for example, by the lead 20' of FIG. 3. Various examples of useful configurations of the non-linear shape are described, for example, in U.S. application Ser. No. 11/413,316, filed Apr. 28, 2006 and entitled "Implantable Medical Leads and Lead Assemblies With Improved Flexibility and Extensibility To Facilitate Body Movements," the teachings of which are incorporated herein by reference.

Methods of making or manufacturing leads in accordance with the present disclosure can be described with reference to the flow diagram of FIG. 4. At step 100, and with additional reference to FIG. 5A, the first and second tubes 22, 24 are initially provided separate from each other. As mentioned above, the tubes 22, 24, as initially provided, may be identical in terms of one or all of material, size, shape, construction, etc. In more general terms, each of the tubes 22, 24, as initially provided may or may not have a definable initial shape. For example, and as shown in FIG. 5A, where the tubes 22, 24 are formed of a soft, pliable material, the tubes 22, 24 can have an observable, generally linear shape in longitudinal extension, it being understood that with these constructions, the tubes 22, 24 are readily transitionable to other shapes. Regardless of whether one or both of the tubes has a discernible initial shape, the initial shape (or lack thereof) differs from the non-linear shape 34 (FIG. 1) subsequently imparted during manufacture. To this end, one or both of the tubes 22 and/or 24 can be provided as having a discrete length, or can be provided in a continuous form (e.g., continuous extrusion).

Returning to FIG. 4, at step 102, the tubes 22, 24 are arranged such that at least a segment 200 of the first tube 22 and a segment 202 of the second tube 24 are arranged side-by-side in longitudinal extension, as in FIG. 5B. In this regard, an entirety of the tubes 22, 24 (in longitudinal extension) can be arranged side-by-side. However, the side-by-side arrangement of at least the segments 200, 202 defines the region of interface 30. At least a portion of the region of interface 30 is forced to the non-linear shape 34 at step 104, and as shown in FIG. 5C.

Figure 6A:
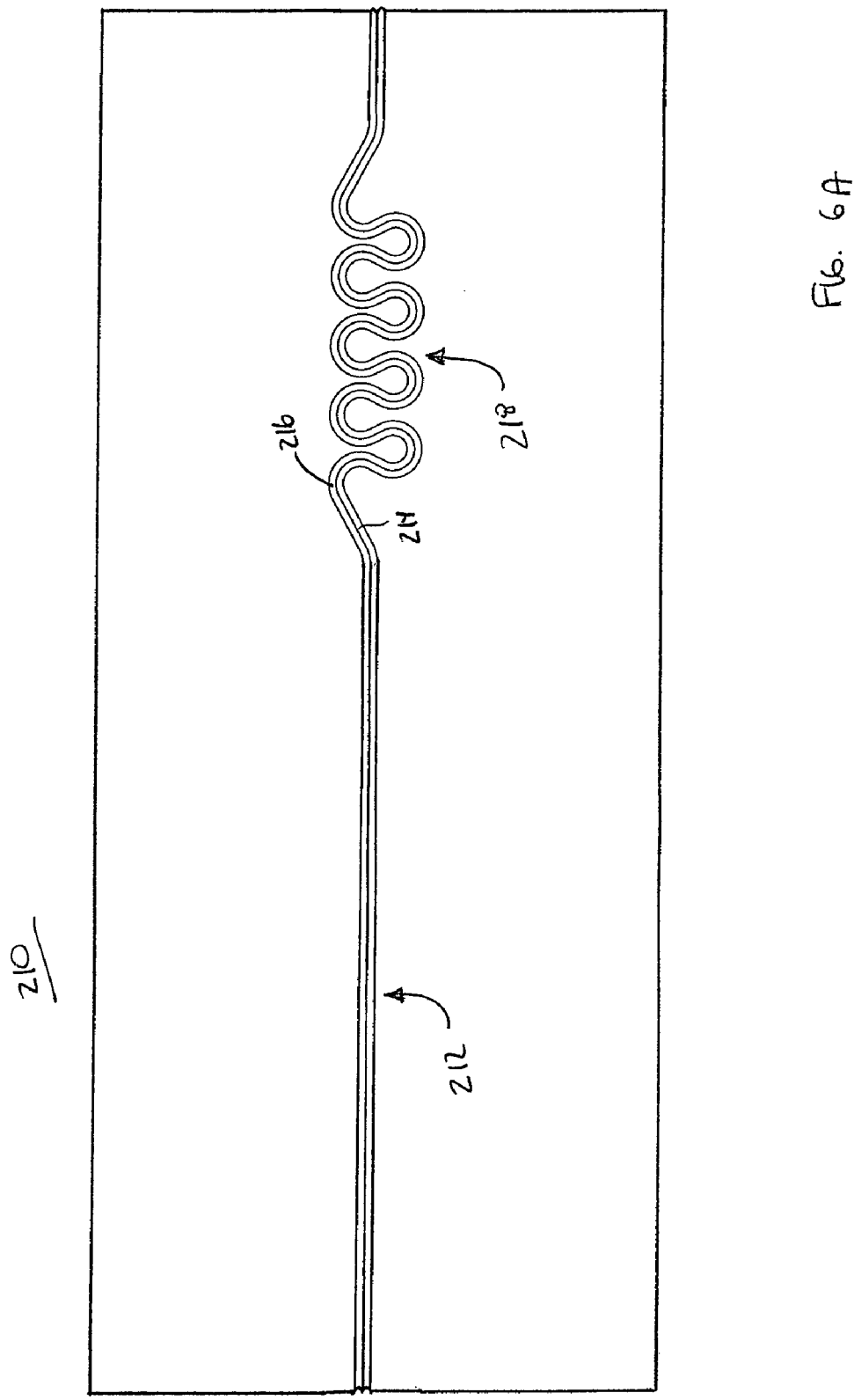
FIG. 6A is a simplified side view of a fixture useful with the methods of FIG. 4.
Figure 6B:
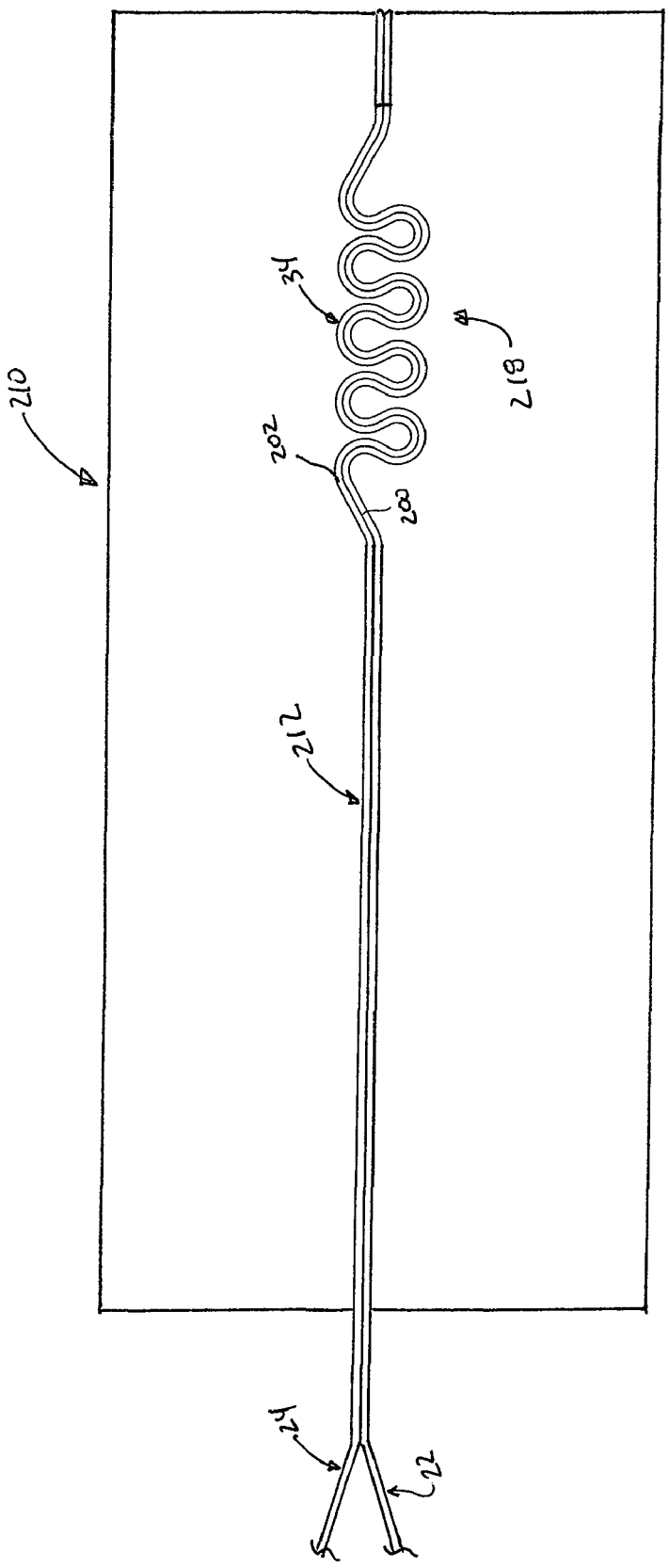
FIG. 6B illustrates use of the fixture of FIG. 6A in connection with the methods of FIG. 4.

Arranging the tubes 22, 24 (step 102) and forcing the tubes 22, 24 to the non-linear shape 34 (step 104) can be accomplished in a variety of fashions, and can occur consecutively, substantially simultaneously, or simultaneously. For example, in some embodiments, methods of the present disclosure include provision of a fixture 210 as shown in FIG. 6A. The fixture 210 can be provided as part of a heat press, and defines or forms a shaping structure 212 sized to receive the tubes 22, 24 (FIG. 5B), and in particular at least the segments 200, 202 (FIG. 5B) thereof. The shaping structure 212 can be appropriately sized cavities 214, 216 for receiving the tubes 22, 24; one or more wires about which the tubes 22, 24 are co-axially mountable; etc. Regardless, the shaping structure 212 includes or defines a non-linear shaped zone 218 corresponding with the desired non-linear shape 34 (FIG. 1), and positions the tubes 22, 24 in a side-by-side relation upon assembly thereto as shown in FIG. 6B. Thus, with embodiments employing the fixture 210 (or similar apparatus), the tube segments 200, 202 (and in some embodiments one or more additional segment(s) of the tubes 22, 24, including entireties of the tubes 22, 24) are mounted to the fixture 210 so as to be side-by-side, and under an environment in which the shaping structure 212 applies a shaping (or holding) force (e.g., a force resisting a natural tendency of the tubes 22, 24 to revert to a more straightened shape) onto the tubes segments 200, 202, forcing the tube segments 200, 202 to the non-linear shape 34. Alternatively, a number of other techniques can be utilized in arranging and shaping the tube segments 200, 202 that may or may not include a fixture or other apparatus that substantially simultaneously performs both steps.

Returning to FIG. 4 and with additional reference to FIG. 7A, the adhesive 26 is applied to at least the side-by-side, non-linearly shaped portion of the tube segments 200, 202 at step 106. In other words, following arranging and shaping of the tube segments 200, 202, the tube segments 200, 202 define the region of interface 30, including the portion 32 thereof having the non-linear shape 34. Due to the side-by-side arrangement of the tubes 22, 24, the region of interface 30 can be viewed as defining first and second opposing major faces 220, 222, as shown in FIG. 7B. Relative to a plane centrally passing through the tubes 22, 24, the opposing major faces 220, 222 are at opposite sides thereof. With these designations in mind, application of the adhesive 26 entails, in some embodiments, dispensing the adhesive 26, in flowable or solution form, from a source (not shown) and onto the first major face 220 such that the applied adhesive directly contacts both of the tubes 22, 24 to effectuate affixment of the tubes 22, 24 to one another, as reflected in FIG. 7C. For example, where the method is performed in conjunction with the fixture 210 (FIG. 6A) as described above, the tube segments 200, 202 remain within the fixture 210, such that the first major face 220 is exposed relative to the fixture 210 and thus available for receiving the adhesive 26. Alternatively, other apparatus(es) can be employed in applying the adhesive 26 to the tube segments 200, 202. In optional embodiments, the adhesive 26 is applied not only to the tube segments 200, 202 otherwise forced to the non-linear shape 34 (FIG. 7A), but also to or along other segments where the tubes 22, 24 are arranged side-by-side.

With reference to FIGS. 4 and 7C, the applied adhesive 26 is allowed or caused to cure at step 108, completing a bond between the adhesive 26 and the tubes 22, 24, and thus affixing the tubes 22, 24 to one another. In some embodiments, the curing step 108 includes subjecting the tubes 22, 24/adhesive 26 to elevated temperatures (i.e., above ambient or normal room temperatures), such as in or on a heat press (not shown). For example, where the fixture 210 (FIG. 6A) is provided as part of a heat press, the heat press, and thus the fixture 210, is heated, with the elevated temperature promoting more rapid curing of the applied adhesive 26. Following curing, a composite structure 230 is formed, including the cured adhesive 26 bonded to the tubes 22, 24, with the tubes 22, 24 being affixed to one another by the cured adhesive 26.

Regardless of whether the tubes 22, 24/adhesive 26 are subjected to an elevated temperature, at optional step 110, an additional amount of the adhesive 26 is applied to the second major face 222. For example, where the method includes use of the fixture 210 (FIG. 6A) as described above, following curing of the adhesive otherwise applied to the first major face 220, the composite structure 230 is turned over relative to the fixture 210, thus positioning the second major face 222 to receive the adhesive 26 (in flowable form) from the adhesive source (not shown). The additional adhesive 26 is cured at the second major face 222 at step 112 as shown in FIG. 7D, such as by subjecting the composite structure 230 to an elevated temperature. As a point of reference, where the methodology employed includes use of heat to promote curing or hardening of the applied adhesive 26, following application of the adhesive 26 to the first major face 220 (step 106) and heating (step 108), for example heating for approximately 10 minutes, the composite structure 230 can be allowed to cool before applying the adhesive 26 to the second major face 222 (step 110) and subsequent heating (step 112), for example heating for approximately 10 minutes. In other embodiments, the adhesive 26 is applied only to the first major face 222, such that optional steps 110 and 112 can be eliminated.

Following bonding of the tubes 22, 24 with the cured adhesive 26, the resultant composite structure 230 is removed from the fixture 210 (FIG. 6A) or any other apparatus used to impart the shaping force on to the tubes 22, 24. In this regard, and as reflected by the illustration of FIG. 7A, the cured adhesive 26 substantially retains the non-linear shape 34 along the portion 32 of the region of interface 30 (e.g., the non-linear shape 34 defined by the portion 32 upon removal of the shaping (or holding) force is within 5% of the non-linear shape imparted by the shaping force in terms of at least one of size, curvature, dimensions, etc.). In other words, upon removal of the shaping force (or in the absence of any external force being applied to the tubes 22, 24), the composite structure 230 (FIG. 7C), and thus the lead 20 (FIG. 1) naturally remains in or retains the non-linear shape 34. As a point of reference, in order for the tubes 22, 24 to straighten out or return to their original, more linear shape, the tubes 22, 24 must strain the adhesive 26. The cured adhesive 26 resists this applied strain, effectively rendering the composite structure 230 to permanently exist in the non-linear shape 34, while capable of elastic deformation. In other words, it is preferable to allow the composite structure 230/lead 20 to extend under low (longitudinally tensioning) load, with the level of extensibility/elastic deformation being selected in accordance with a desired end use. For example, where the lead 20 is to be implanted in a neck region of a patient, the lead 20, and in particular the portion 32 having the non-linear shape 34, exhibits a longitudinal extensibility of approximately 40% when subjected to a load force of 0.1 lbs or less. In other embodiments, the selected adhesive 26, as well as other processing parameters, can be altered to generate differing extensibility characteristics, such as higher or lower extensibility under higher or lower load values. Regardless, the cured adhesive 26 alone provides this elastically deformable, shape memory attribute.

At step 114, a conductive element is disposed within at least one of the tubes 22 or 24. For example, the tubes 22, 24 can remain with the fixture 210 (FIG. 6A) and the conductive element 28a (FIG. 1) fed through the first tube 22; where desired, the second conductive element 28b (FIG. 1) can also be provided and fed through the second tube 24 (it being recalled that in some embodiments, only one of the conductive elements 28a or 28b is provided). Notably, while the method has been described as entailing assembly of the conductive element(s) 28a, 28b after completion of the adhesive application and curing processes, in other embodiments, the conductive element(s) 28a, 28b can be associated with the corresponding tube 22 or 24 in question prior to arranging the tubes 22, 24 (step 102); prior to forcing the tube segments 220, 222 to the non-linear shape 34 (step 104); prior to applying the adhesive 26 (step 106); or prior to curing the adhesive 26 (step 108). For example, the conductive element 28a can be disposed within the first tube 22 as the first tube 22 is initially provided (e.g., slid within the tube 22; the tube 22 extruded about the conductive element 28a; the tube 22 molded about the conductive element 28a such that the conductive element 28a is encompassed within a thickness of the tube 22; etc.), followed by subsequent arranging of the tube segments 220, 222 in a side-by-side relationship, etc.

Regardless of the point at which the conductive element(s) 28a, 28b is disposed within the corresponding tube 22, 24, the resultant lead 20 has the shape memory and extensibility characteristics described above due, at least primarily, to the cured adhesive 26. That is to say, while the conductive element(s) 28a, 28b may contribute to shape memory and/or extensibility, the cured adhesive 26 is capable of generating the desired properties alone. In fact, where the conductive element(s) 28a, 28b exhibit a spring-back properties, the cured adhesive 26 resists this inherent force in substantially maintaining the non-linear shape 34 as above. Where desired, one or more additional, optional shaping elements may be included with the lead 20 in some alternative embodiments, as described in U.S. patent application Ser. No. 11/413,316, filed Apr. 28, 2006 and entitled "Implantable Medical Leads and Lead Assemblies With Improved Flexibility and Extensibility To Facilitate Body Movements."

Following manufacture and with reference to FIG. 1, the lead 20 can be implanted using any acceptable technique and at any bodily location. The implanted lead 20 will readily longitudinally extend in the presence of an applied tensioning load (e.g., a pulling force applied at the conductive lead termination end 42) as the lead 20 "expands" along the portion 32 having the non-linear shape 34 (e.g., the sigmoid shape 34 in accordance with some embodiments permits or experiences a longitudinal increase in linear length as the curves 60 slightly or overtly open or spread, thus becoming more straightened). Upon removal of the tensioning load, the lead 20 reverts back toward the non-linear shape 34 due, at least primarily, to the cured adhesive 26 (and its inherent resistance to the strain generated by or upon the tubes 22, 24).

Figure 8:
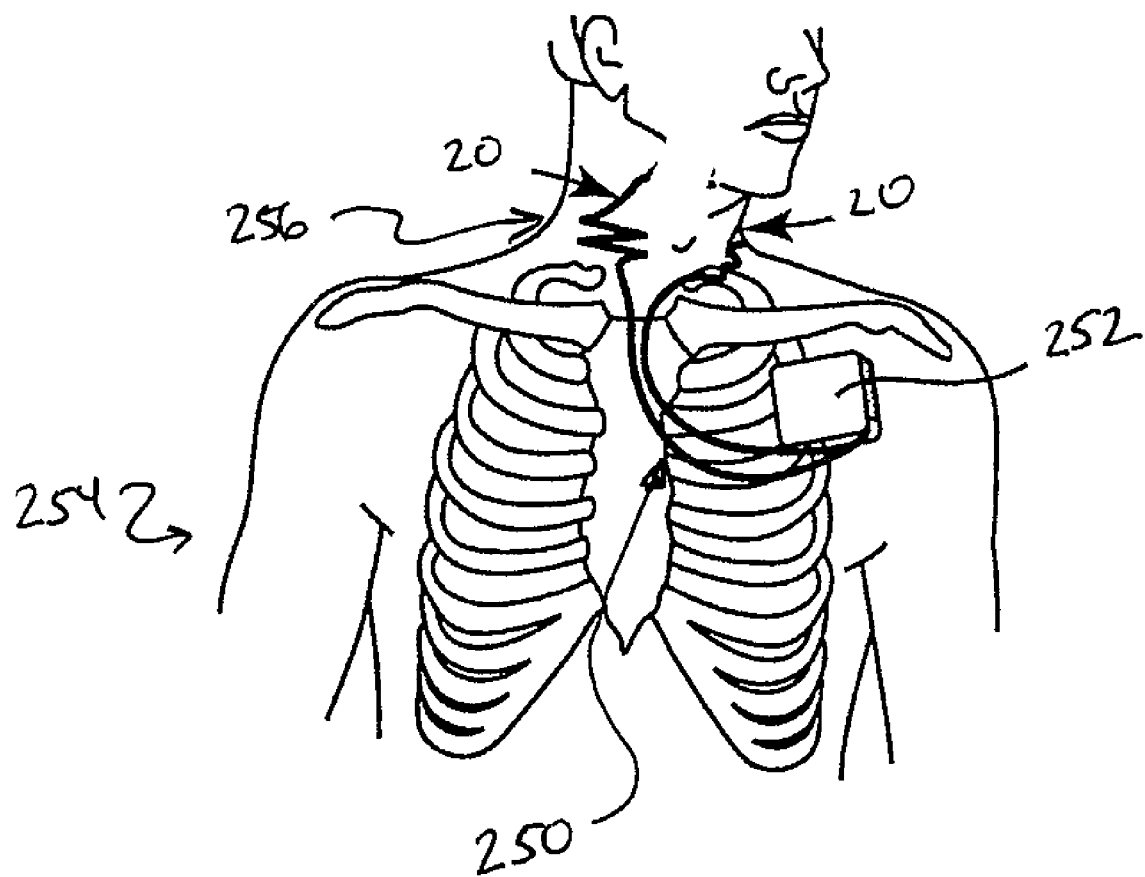
FIG. 8 is a simplified illustration of a patient to which a system including a lead in accordance with aspects of the present disclosure is implanted.

One useful application of the lead 20 is as part of an implantable stimulation system 250 as shown in FIG. 8. The system 250 can include one or more of the leads 20, along with an implantable signal generator 252 of a type known in the art. The system 250 can be implanted at various regions of a patient 254, and in some embodiments is implanted and employed to effectuate electrical stimulation treatments in a neck region 256 of the patient 254. Such a system 250 can be employed to treat such maladies as dysphagia, although this implantation location and treatment are non-limiting examples. The lead 20 can be implanted at virtually any bodily region, and can in other embodiments be used externally. Similarly, the lead 20 can be used to effectuate a wide variety of other treatments. Regardless, the lead 20 operates to deliver electrical energy to or from the signal generator 252, and deforms and re-forms in the manners described above when the patient 254 physically moves the region of implant.

Although the present invention has been described with reference to preferred embodiments, workers skilled in the art will recognize that changes can be made in form and detail without departing from the spirit and scope of the present invention.

What is claimed is:

1. A method of making an implantable medical lead, the method comprising:
    providing a first tube;
    providing a second tube;
    arranging the tubes such that a segment of the first tube and a segment of the second tube are side-by-side along a region of interface, wherein the region of interface is defined by first and second major faces at opposite sides, respectively, of a plane passing centrally through the side-by-side tube segments;
    forcing the tubes to a non-linear shape along at least a portion of the region of interface;
    applying adhesive to the portion of the region of interface, wherein applying the adhesive includes dispensing the adhesive on the first major face;
    curing the adhesive to bond the tubes to one another with the adhesive along the portion of the region of interface, wherein curing comprises subjecting the region of interface to a temperature above ambient for a first time period, wherein upon curing, the adhesive substantially maintains the non-linear shape of the portion of the region of interface in the absence of an external force;
    applying the adhesive on the second major face after the first time period;
    curing the adhesive on the second major face; and
    disposing a conductive element within at least one of the first and second tubes.

2. The method of claim 1, wherein curing the adhesive on the second major face includes: subjecting the region of interface to a temperature above ambient for a second time period to promote curing of the adhesive at the second major face.

* * * * *